(12) United States Patent
Amin et al.

(10) Patent No.: US 9,192,876 B2
(45) Date of Patent: Nov. 24, 2015

(54) SEPARATION OF LIGHT HYDROCARBONS AND SOUR SPECIES FROM A SOUR GAS

(75) Inventors: Robert Amin, Salter Point (AU);
Ahmed Barifcani, Perth (AU)

(73) Assignee: IOR Technology PTY Ltd., Perth (AU)

( * ) Notice: Subject to any disclaimer, the term of this patent is extended or adjusted under 35 U.S.C. 154(b) by 948 days.

(21) Appl. No.: 13/390,902

(22) PCT Filed: Aug. 19, 2010

(86) PCT No.: PCT/AU2010/001062
§ 371 (c)(1),
(2), (4) Date: Jun. 5, 2012

(87) PCT Pub. No.: WO2011/020150
PCT Pub. Date: Feb. 24, 2011

(65) Prior Publication Data
US 2012/0233920 A1   Sep. 20, 2012

(30) Foreign Application Priority Data
Aug. 21, 2009 (AU) ................................ 2009903991

(51) Int. Cl.
*B01D 3/14* (2006.01)
*C07C 7/06* (2006.01)
(Continued)

(52) U.S. Cl.
CPC *B01D 3/145* (2013.01); *B01D 3/36* (2013.01); *C07C 7/05* (2013.01); *C07C 7/06* (2013.01); *C10L 3/10* (2013.01); *Y02C 10/06* (2013.01); *Y02C 20/20* (2013.01)

(58) Field of Classification Search
CPC ... B01D 3/143; B01D 3/36; C07C 7/04–7/06; C07C 9/06; C10L 3/10; Y02C 10/06; Y02C 20/20
USPC .................. 202/158–162; 203/57, 59, 63
See application file for complete search history.

(56) References Cited

U.S. PATENT DOCUMENTS

| | | | | |
|---|---|---|---|---|
| 4,246,015 A | * | 1/1981 | Styring, Jr. | ..................... 62/629 |
| 4,311,495 A | * | 1/1982 | Styring, Jr. | ..................... 62/625 |

(Continued)

FOREIGN PATENT DOCUMENTS

| | | |
|---|---|---|
| CA | 1297398 | 3/1992 |
| EP | 0036733 A1 | 9/1981 |

OTHER PUBLICATIONS

Supplementary European Search Report, Application No. EP10809366, issued by the European Patent Office, date completed Jun. 28, 2013, 7 pages.

(Continued)

*Primary Examiner* — In Suk Bullock
*Assistant Examiner* — Jonathan Miller
(74) *Attorney, Agent, or Firm* — Haynes and Boone, LLP

(57) ABSTRACT

A process for recovering a light hydrocarbon, such as ethane, from a sour hydrocarbon gas. The process involves mixing the sour hydrocarbon gas with an azeotrope inhibitor and then passing the mixture into a first distillation column. The first distillation column is operated under a set of temperature and pressure conditions in which the light hydrocarbon is substantially separated from the mixture as an overhead vapor product. The sour species in the mixture can be recovered by passing the bottoms liquid product into a second distillation column under a second set of temperature and pressure conditions in which the sour species is separated as a second overhead vapor product.

20 Claims, 2 Drawing Sheets

(51) Int. Cl.
  *B01D 3/36* (2006.01)
  *C07C 7/05* (2006.01)
  *C10L 3/10* (2006.01)

(56) References Cited

U.S. PATENT DOCUMENTS

| | | | | |
|---|---|---|---|---|
| 4,374,657 | A | * | 2/1983 | Schendel et al. ............... 62/624 |
| 4,462,814 | A | * | 7/1984 | Holmes et al. .................. 62/625 |
| 4,675,035 | A | * | 6/1987 | Apffel ............................. 62/625 |
| 4,717,408 | A | * | 1/1988 | Hopewell ........................ 62/633 |
| 4,793,841 | A | | 12/1988 | Burr |
| 4,976,849 | A | | 12/1990 | Soldati |
| 6,436,174 | B1 | * | 8/2002 | Grossmann et al. ............ 95/191 |
| 2009/0259082 | A1 | * | 10/2009 | Deluga et al. ................... 585/14 |
| 2011/0138854 | A1 | * | 6/2011 | Huang et al. .................... 62/630 |

OTHER PUBLICATIONS

International Search Report, Date of Completion Sep. 21, 2010, 5 pages, PCT/AU2010/001062, Australian Patent Office.
International Preliminary Report on Patentability, Date Completed Jul. 7, 2011; 13 pages, PCT/AU2010/001062, Australian Patent Office.

* cited by examiner

SEPARATION OF LIGHT HYDROCARBONS AND SOUR SPECIES FROM A SOUR GAS

BACKGROUND OF THE INVENTION

The present application is the U.S. national-stage of PCT International Patent Application No. PCT/AU2010/001062, filed Aug. 19, 2010, which claims priority to Australia Patent Application No. 2009903991, filed Aug. 21, 2009; the disclosure of each of which is specifically incorporated herein in its entirety by express reference thereto.

FIELD

The present invention relates to a process for recovering a light hydrocarbon from a sour gas, in particular to a process for recovering methane and ethane from a hydrocarbon gas containing carbon dioxide and/or hydrogen sulphide. Additionally, the present invention relates to a process for recovering high purity sour species from a sour gas. Further, the present invention also broadly relates to a process for inhibiting formation of an azeotrope, and more particularly to a process for inhibiting formation of a carbon dioxide-ethane azeotrope in a sour gas.

BACKGROUND

Carbon dioxide and/or hydrogen sulphide are common contaminants of natural gas which must be removed in a process known as "sweetening". Ethane is a major component of natural gas streams and it forms an azeotrope with carbon dioxide under pressure and at low temperature which hinders carbon dioxide separation. While it is possible to separate carbon dioxide from the methane and higher hydrocarbon fractions of natural gas, respectively, by distillation, it is difficult to separate carbon dioxide from the ethane fraction. Ethane may also form an azeotrope with hydrogen sulphide, as will propane, with the same problems evident.

Recovery and separation of ethane from carbon dioxide is important in the gas industry because if it is not separated, substantial quantities of ethane gas are wasted if the separated carbon dioxide stream containing the azeotrope is vented to atmosphere or further treated for sequestration purposes.

Traditional techniques (e.g., chemical absorption using amine solutions and adsorption using molecular sieves), for breaking the carbon dioxide/ethane azeotrope are capital intensive and require complex process control. The present invention seeks to overcome at least some of the aforementioned disadvantages.

Accordingly, there is a need to provide a process for recovering valuable gases from sour gas mixtures, in particular for recovering ethane from a hydrocarbon gas containing carbon dioxide and/or hydrogen sulphide. Additionally, there is a need to provide a process for substantially removing hydrogen sulphide and carbon dioxide from a sour gas and recovering high purity carbon dioxide therefrom.

SUMMARY

In its broadest aspect, the invention provides a process for recovering a light hydrocarbon from a sour hydrocarbon gas, in particular methane and ethane from a hydrocarbon gas containing carbon dioxide and/or hydrogen sulphide. The invention also provides a process for inhibiting formation of an azeotrope in a mixture under temperature and pressure conditions in which said azeotrope would be expected to form. In particular, the invention provides a process for inhibiting formation of a sour species-ethane azeotrope in a hydrocarbon gas. The invention further provides a process for recovering high purity carbon dioxide or hydrogen sulphide from a sour hydrocarbon gas.

Accordingly in a first aspect of the present invention there is provided a process for recovering a light hydrocarbon from a sour hydrocarbon gas, the process comprising the steps of:
  a) mixing the sour hydrocarbon gas with an azeotrope inhibitor; and
  b) passing the mixture into a first distillation column and operating the first distillation column under a set of temperature and pressure conditions in which the light hydrocarbon is substantially separated from the mixture as an overhead vapour product.

In a second aspect of the present invention there is provided a process for recovering sour species from a sour hydrocarbon gas, the process comprising the steps of:
  a) mixing sour hydrocarbon gas with an azeotrope inhibitor;
  b) passing the mixture into a first distillation column and operating said first distillation column under a first set of temperature and pressure conditions in which the light hydrocarbon is substantially separated from the mixture as a first overhead vapour product; and
  c) separating the sour species from a bottoms liquid product of the first distillation column.

In one embodiment, the step of separating the sour species from said bottoms liquid product comprises passing said bottoms liquid product into a second distillation column and operating said second distillation column under a second set of temperature and pressure conditions in which the sour species is separated from the bottoms liquid product as a second overhead vapour product.

In an alternative embodiment, the step of separating the sour species from said bottoms liquid product comprises reducing the pressure of the bottoms liquid product to a pressure at which the sour species is separated from the bottoms liquid product in a vapour phase and said agent remain substantially in a liquid phase. In this way, said agent may be recovered and subsequently re-used in step a).

The azeotrope inhibitor agent is an inorganic compound or an organic compound that disrupts or inhibits formation of an azeotrope formed by a sour species and a light hydrocarbon.

Such compounds may demonstrate a molecular structure similar to the molecular structure of the sour species, such that the agent is capable of displacing the sour species from said azeotrope.

In one embodiment, the agent has critical properties close to critical properties of a sour species in the sour hydrocarbon gas.

In one embodiment, the agent is capable of broadening a liquid-gas phase region of each of the components in the azeotrope to an extent where under pressure and temperature conditions where the azeotrope would be expected to form, a first component of the azeotrope may exist in a vapour phase and the other of the components of the azeotrope and the agent may exist in a liquid phase. In one form of the invention, the agent is capable of absorbing the other of the components of the azeotrope when in the liquid phase.

In one form of the invention, the agent is a gas having a boiling point located intermediate the respective boiling points of methane and said azeotrope. In one preferred embodiment, the agent comprises ethylene oxide. In another preferred embodiment, the agent comprises 1,1-dimethylhydrazine.

Said agent may be added in an amount sufficient to inhibit formation of or disrupt the light hydrocarbon-sour species azeotrope at the temperature and pressure conditions under which said azeotrope would be expected to form.

In one embodiment of the invention, said hydrocarbon gas is mixed with about 1 mol % to about 40 mol % of the agent, preferably about 1 mol % to about 20 mol %, even more preferably 1.5 mol % to 5 mol %.

Advantageously, mixing said agent with the sour hydrocarbon gas facilitates operation of the first and second distillation columns at higher temperatures than would otherwise be used for separation of the light hydrocarbon and/or sour species from the sour hydrocarbon gas, thereby avoiding a temperature region in which solids of the sour species form.

In one embodiment of the invention the recovery of the light hydrocarbon from the first distillation column is greater than 80 mol %, preferably greater than or equal to 90 mol %.

In another embodiment of the invention, the separation of sour species may be about 90 mol %, preferably greater than or equal to 95 mol %.

In a further embodiment, a purity of the separated sour species may be about 90 mol % or greater.

In one form of the invention, the agent may be mixed with the sour hydrocarbon gas prior to passing the mixture to the first distillation column. In another form of the invention, the agent may be mixed with the sour hydrocarbon gas within the first distillation column by introducing the sour hydrocarbon gas and the agent separately into the first distillation column. It will be appreciated that in alternative embodiments the agent may be mixed with the sour hydrocarbon gas at other stages of the process.

Advantageously, the inventors of the present invention have also found that the removal of C3+ hydrocarbons from the sour stream prior to mixing with said agent, not only improves the respective recoveries of both light hydrocarbon and sour species from the sour hydrocarbon gas but a reduced molar percentage of agent may be used in the mixture to disrupt or inhibit formation of the sour species-light hydrocarbon azeotrope.

Accordingly, in a preferred embodiment, the process further comprises separating C3+ hydrocarbons from the sour hydrocarbon gas prior to mixing the agent with the sour hydrocarbon gas.

In another aspect of the invention there is provided a process for recovering sour species from a sour hydrocarbon gas, the process comprising the steps of:
  a) separating C3+ hydrocarbons from the sour hydrocarbon gas;
  b) mixing the C3+ hydrocarbon-depleted gas with an azeotrope inhibitor;
  c) passing the mixture into a first distillation column and operating said first distillation column under a first set of temperature and pressure conditions in which the light hydrocarbon is substantially separated from the mixture as a first overhead vapour product; and
  d) separating the sour species from a bottoms liquid product of the first distillation column.

In one form of the invention, substantially separating C3+ hydrocarbons comprises passing the sour hydrocarbon gas into a distillation column and operating said distillation column under a set of temperature and pressure conditions sufficient to effect substantial separation of C3+ hydrocarbons as a liquid bottoms product of the distillation column. Generally, said conditions are selected so that no more than about 0.2 mol % of C3+ hydrocarbons remain in the overhead vapour product of said distillation. Preferably said conditions are selected such that the concentration of sour species in the separated C3+ hydrocarbon stream may be no more than about 0.01 mol %.

Removal and separation of light hydrocarbons such as ethane and propane from sour hydrocarbon gas may be hindered by formation of light hydrocarbon-sour species azeotropes under certain temperature and pressure conditions. Advantageously, the inventors have found that mixing the sour hydrocarbon gas with an azeotrope inhibitor agent inhibits the formation of or disrupts light hydrocarbon-sour species azeotropes.

Accordingly, in another aspect of the present invention there is provided a process for inhibiting formation of or disrupting an azeotrope in a mixture having a composition capable under sufficient temperature and pressure conditions of forming said azeotrope, the process comprising mixing the mixture with an agent having critical properties close to the critical properties of one of the azeotropic species.

In a further aspect of the present invention there is provided a process for inhibiting formation of or disrupting a sour species-light hydrocarbon azeotrope in a sour hydrocarbon gas, the process comprising mixing said hydrocarbon gas with an agent having critical properties close to critical properties of the sour species in said gas.

When the sour species is carbon dioxide, the light hydrocarbon capable of forming said azeotrope with carbon dioxide is ethane. When the sour species is hydrogen sulphide, the light hydrocarbon capable of forming said azeotrope with hydrogen sulphide is ethane or propane.

The recovery of carbon dioxide in a substantially pure form suitable to store and/or sequester by the process defined above facilitates a relative reduction in greenhouse gas emissions in comparison to prior art processes in which the carbon dioxide content of the gas stream would be vented to the atmosphere or flared.

According to a fourth aspect of the invention there is provided a method of creating a financial instrument tradable under a greenhouse gas Emissions Trading Scheme (ETS), the method comprising the step of exploiting a process for process for recovering sour species from a sour hydrocarbon gas, defined by the second aspect of the invention, wherein he sour species is a greenhouse gas.

In one embodiment of the invention, the financial instrument comprises one of either a carbon credit, carbon offset or renewable energy certificate.

BRIEF DESCRIPTION OF THE FIGURES

Preferred embodiments of the present invention will now be described, by way of example only, with reference to the accompanying figures, in which.

DESCRIPTION OF A PREFERRED EMBODIMENT

In the description of the Figures reference is made to a natural gas stream as an example of the gas stream that may be treated in the process according to the present invention. It will be appreciated, however, that the gas stream may be any stream of gas that comprises hydrocarbons, carbon dioxide, hydrogen sulphide, and other sour species. Illustrative examples of such gas streams include, but are not limited to, natural gas, coal seam gas, associated gas, landfill gas, and biogas. The composition of the gas stream may vary significantly but the gas stream will generally contain methane, ethane, propane, higher hydrocarbons (C3+), water, carbon dioxide, hydrogen sulphide, and other sour species. The term "sour species" means any one or more of carbon dioxide, hydrogen sulphide, carbon disulfide, carbonyl sulphide, mercaptans (R—SH, where R is an alkyl group having one to 20 carbon atoms), sulphur dioxide, aromatic sulphur-containing compounds, and aromatic hydrocarbons such as benzene, toluene, xylene, naphthalenes, and so forth.

It will be also understood that while the following description refers to specific sequences of process steps, pieces of apparatus and equipment and their configuration to perform such processes in relation to particular gas compositions, operating pressures and temperatures, and so forth, such detail is provided for illustrative purposes only and is not intended to limit the scope of the present invention in any way.

Figure 1:
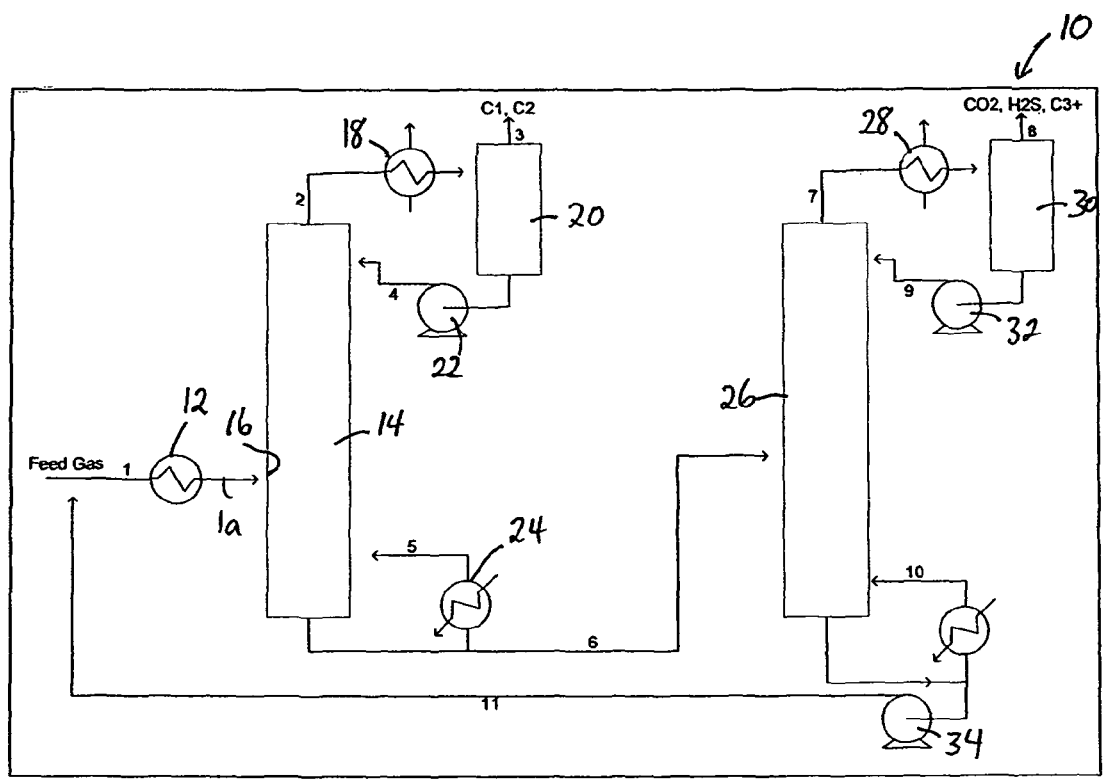
FIG. 1 shows a process flow diagram in accordance with one embodiment of the present invention whereby an agent for inhibiting formation of, or disrupting, a light hydrocarbon-sour species azeotrope is mixed with a feed stream containing carbon dioxide.

Referring to FIG. 1, in accordance with various aspects of the present invention, there is shown an apparatus 10 for performing the process of the present invention.

Prior to undergoing the processes of the present invention, the gas stream will have been dehydrated by any suitable dehydration process as will be known to those skilled in the art.

A feed gas containing methane, ethane, carbon dioxide, hydrogen sulphide, propane, and heavier hydrocarbons with an illustrative composition as indicated in Table 1 is capable of forming a light hydrocarbon-sour species azeotrope, in particular an ethane-carbon dioxide azeotrope, under high pressure and low temperature conditions.

TABLE 1

| Component | Mol % |
| --- | --- |
| Methane | 72 |
| Ethane | 5 |
| Carbon Dioxide | 15 |
| Hydrogen Sulphide | 3 |
| Propane | 3 |
| Isobutane | 1.5 |
| Tert-butane | 0.4 |
| Isopentane | 0.1 |

In accordance with the present invention, the feed gas was mixed with about 15% to about 40 mol % of an azeotrope inhibitor agent for inhibiting formation of, or disrupting, the ethane-carbon dioxide azeotrope at the temperature and pressure conditions under which said azeotrope would be expected to form. In this particular embodiment the agent comprises 1,1-dimethyl hydrazine.

The mixture is introduced under pressure of about 55 bar to the apparatus 10 via line 1 and passed to a chiller 12 where the mixture is cooled to about −50° C. and partially condensed. The partially condensed mixture then enters a first distillation column 14 at feed tray 16 through line 1a.

The first distillation column 14 contains a plurality of vapour-liquid contact devices such as trays or packing. The number of such contact devices required in the distillation column depends on the required operating conditions and may be readily determined by a person skilled in the art. In this particular embodiment, the first distillation column 14 contains 23-45 trays with feed tray 16 being located intermediate a bottom and top tray of the first distillation column 14.

Generally, the first distillation column 14 may be operated at a pressure of about 50 to about 57 bar with a top temperature of about −64° C. to about −68° C. and a bottom temperature in a range of about 75° C. to about 166° C., preferably in a range of about 90° C. to about 120° C.

Upon entry to the first distillation column, methane and ethane contained in the mixture are flashed off as a vapour stream. The vapour stream exits the first distillation column 14 through line 2 and enters an overhead chiller 18 where it is partially condensed and introduced to vapour-liquid separator 20. Resulting overhead vapour product which is rich in methane and ethane is separated in separator 20 and leaves the apparatus 10 under pressure through line 3. Any resulting condensate is pumped back to the top tray of the first distillation column 14 by pump 22 via line 4.

A liquid stream from the first distillation column 14 is partially reboiled by reboiler 24 and returned to the first distillation column 14 by line 5.

A liquid bottoms product from the first distillation column 14 is passed via line 6 to a second distillation column 26 operating at a lower pressure in a pressure range of about 35 to about 42 bar. Typically, the second distillation column 26 contains about 10 trays and is arranged to receive liquid feed at about the seventh tray thereof.

Overhead vapours containing carbon dioxide, hydrogen sulphide, propane and heavier hydrocarbons exit the second distillation column 26 through line 7 where they are cooled to about 35° C. by cooler 28 and partially condensed. The resulting liquid-vapour mixture is directed to separator 30. Condensate separated in separator 30 is pumped back to the top tray of the second distillation column 26 by pump 32 via line 9.

The overhead vapour stream separated in separator 30 contains carbon dioxide, hydrogen sulphide, propane and heavier hydrocarbons. Said stream may be passed via line 8 to a further distillation column (not shown) operating a lower pressure regime of about 10-12 bar and a top temperature of −37° C. and 45° C. for the bottom stream. Under these operation conditions, propane and the heavier hydrocarbons may be separated from the carbon dioxide and hydrogen sulphide sour species, such that the concentration of hydrogen sulphide in the C3+ hydrocarbons is about 100 ppm.

The bottoms liquid stream from the second distillation column 26 comprises about 96 mol % 1,1-dimethyl hydrazine and may be returned through line 11 via pump 34 for mixing with feed gas.

The recovery of methane, ethane, and carbon dioxide (mol %) in the overhead vapour products of the first and second distillation columns 14, 26, respectively and the dependence on the molar percentage of 1,1-dimethyl hydrazine in the feed gas-agent mixture is shown in Table 2 for illustrative purposes.

TABLE 2

| 1,1-dimethyl hydrazine in feed gas (mol %) | Methane recovery (mol %) | Ethane recovery (mol %) | Carbon Dioxide recovery (mol %) |
| --- | --- | --- | --- |
| 40 | 92.7 | 82 | 90 |
| 20 | 93.15 | 90 | 95 |
| 15 | 93.1 | 92 | 95 |

Figure 2:
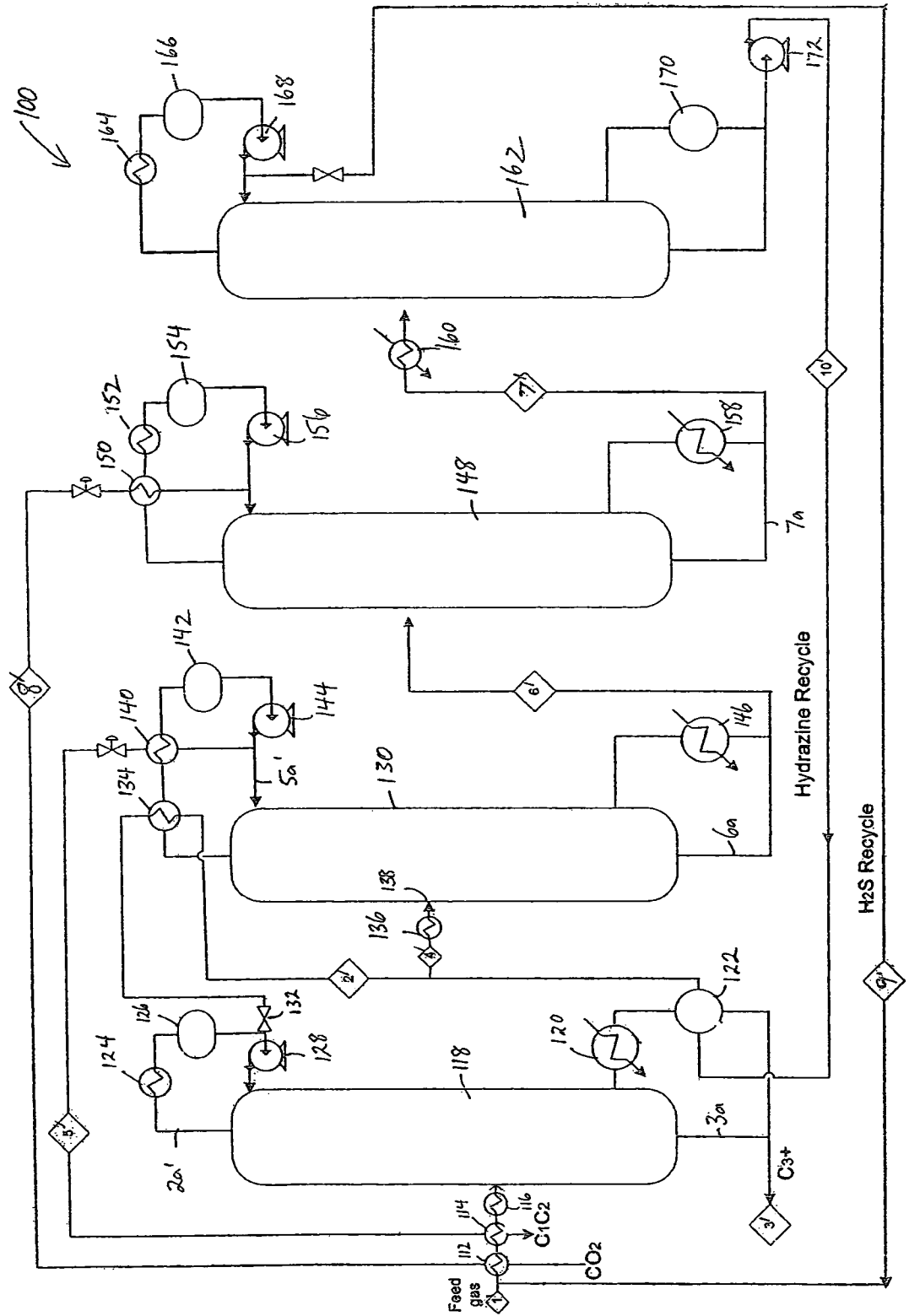
FIG. 2 shows a process flow diagram in accordance with another embodiment of the present invention whereby 20 mol % said agent is mixed with a feed stream containing carbon dioxide and about 20 mol % hydrogen sulphide after C3+ hydrocarbons have been substantially distillatively separated therefrom.

Referring now to FIG. 2, there is shown an apparatus 100 for performing a further embodiment of the process of the present invention, wherein the process further comprises separating C3+ hydrocarbons from the feed gas prior to mixing a C3+ hydrocarbon-depleted feed gas with said agent. The inventors have found that prior removal of C3+ hydrocarbons not only improves the respective recoveries of both light hydrocarbon and sour species from the sour hydrocarbon stream, but a reduced molar percentage of agent may be used in the mixture to disrupt or inhibit formation of the sour species-light hydrocarbon azeotrope.

A feed gas containing methane, ethane, C3+ hydrocarbons, about 5 mol % carbon dioxide and from about 0.2 mol % to about 20 mol % hydrogen sulphide is introduced under pressure of about 38 bar to the apparatus 100 via line 1' and successively cooled in feed gas pre-cooler 112, cooler 114, and chiller 116 to about −53° C., at which temperature the feed gas partially condenses.

The partially condensed feed gas is passed into a distillation column 118 operated under a first set of temperature and pressure conditions arranged to substantially separate and recover C3+ hydrocarbons as a liquid bottoms product thereof. In this particular embodiment, distillation column 118 is operated at 36 bar pressure with a top temperature of about −82° C. and a bottom temperature of about 114° C.

A liquid stream from distillation column 118 is partially reboiled by first reboiler 120 and second reboiler 122 and returned to distillation column 118 by line 3a'. A liquid bottoms product substantially comprising C3+ hydrocarbons with 0.01 mol % hydrogen sulphide from distillation column 118 exits the apparatus 100 via line 3'.

A vapour stream from distillation column 118 is withdrawn therefrom via line 2a' and passed to an overhead condenser 124 where it is partially condensed and thence to a vapour-liquid separator 126. Any condensate is pumped back to the top tray of the distillation column 118 by pump 128. A resulting C3+ hydrocarbon-depleted vapour stream is separated in separator 126 and passed to a first distillation column 130 via line 2'.

To conserve energy within the apparatus 100 the C3+ hydrocarbon-depleted vapour stream may be cooled by expanding said stream in expander 132, and said cooled stream may be passed through an overhead chiller 134 of the first distillation column 130 for use therein as a cooling stream.

Prior to introducing the C3+ hydrocarbon-depleted vapour stream to the first distillation column 130, said stream is mixed with an agent to inhibit formation of, or disrupt, a light hydrocarbon-sour species azeotrope which would be expected to form under the operating conditions of the first distillation column 130, given the composition of the C3+ hydrocarbon-depleted vapour stream. In this particular embodiment, the mixture comprises from 5-20 mol % 1,1-dimethylhydrazine.

The mixture is cooled in chiller 136 and introduced to the first distillation column 130 via feed tray 138. In this particular embodiment the first distillation column 130 may be operated at a pressure of about 56 bar with a top temperature of about −64° C. and a bottom temperature of about 116° C.

In the first distillation column 130, methane and ethane contained in the mixture are flashed off as a vapour stream. The vapour stream exits the first distillation column 130 and is successively cooled by passing through overhead chiller 134 and overhead condenser 140 where it is partially condensed and introduced to vapour-liquid separator 142. The resulting overhead vapour product separated in separator 142 comprises about 99 mol % combined methane and ethane. The combined methane-ethane stream may be used as a cooling stream in the overhead condenser 140 and cooler 114 before exiting the apparatus 100 via line 5'.

Any resulting condensate is pumped back to the top tray of the first distillation column 130 by pump 144 via line 5a'.

A liquid stream from the first distillation column 130 is partially reboiled by reboiler 146 and returned to the first distillation column 130 by line 6a'. The resulting liquid bottoms product comprises said agent, carbon dioxide and hydrogen sulphide.

The liquid bottoms product from the first distillation column 130 is passed via line 6' to a second distillation column 148 operating at about 35 bar with a top temperature of about −2.4° C. and a bottom temperature of about 202° C.

Overhead vapours exit the second distillation column 148 through line 8a' where they are successively cooled and at least partially condensed in chiller 150 and condenser 152. The resulting liquid-vapour mixture is directed to separator 154 where condensate separated in separator 154 is pumped back to the top tray of the second distillation column 148 by pump 156.

The overhead vapour stream separated in separator 30 substantially comprises at least 90 mol % carbon dioxide. Said stream may be passed out of the apparatus via line 8' after being used as a cooling stream in chiller 150 and pre-cooler 112.

A liquid stream from the second distillation column 148 is partially reboiled by reboiler 158 and returned to the second distillation column 148 by line 7a'. The resulting liquid bottoms product from the second distillation column 148 comprises said agent and hydrogen sulphide.

The liquid bottoms product from the second distillation column 148 is passed via line 7' to a cooler 160 and before being introduced to a third distillation column 162 operating at about 33 bar with a top temperature of about 38° C. and a bottom temperature of about 203° C.

Overhead vapours exit the third distillation column 162 through line 9a' where they are at least partially condensed in condenser 164. The resulting liquid-vapour mixture is directed to separator 166 where condensate separated in separator 166 is pumped back to the top tray of the third distillation column 162 by pump 168.

The overhead vapour product stream separated in separator 166 substantially comprises hydrogen sulphide. Said stream may be recycled within the apparatus 100 after being used as a cooling stream in condenser 140.

A liquid stream from the third distillation column 162 is partially reboiled by reboiler 170 and returned to the third distillation column 162 by line 10a'.

The bottoms liquid stream from the third distillation column 162 comprises about 99 mol % 1,1-dimethyl hydrazine and may be recycled through line 10' via pump 172 for mixing with the C3+ hydrocarbon-depleted feed stream.

As will be evident from the foregoing description, the process of the present invention facilitates a reduction of greenhouse gas emissions in comparison with conventional technologies for sweetening sour gas streams.

A financial instrument tradable under a greenhouse gas Emissions Trading Scheme (ETS) may be created by exploitation a gas sweetening plant employing the processes of the present invention. The instrument may be, for example, one of either a carbon credit, carbon offset or renewable energy certificate. Generally, such instruments are tradable on a market that is arranged to discourage greenhouse gas emission through a cap and trade approach, in which total emissions are 'capped', permits are allocated up to the cap, and trading is allowed to let the market find the cheapest way to meet any necessary emission reductions. The Kyoto Protocol and the European Union ETS are both based on this approach. One example of how credits may be generated by using the gas liquefaction plant follows. A person in an industrialised country wishes to get credits from a Clean Development Mechanism (CDM) project, under the European ETS. The person contributes to the establishment of a gas sweetening plant comprising a gas sweetening plant employing the processes of the present invention. Credits (or Certified Emission Reduction Units where each unit is equivalent to the reduction of one metric tonne of $CO_2$ or its equivalent) may then be issued to the person. The number of CERs issued is based on the monitored difference between the baseline and the actual emissions. It is expected by the applicant that offsets or credits of a similar nature to CERs will be soon available to persons investing in low carbon emission energy generation in industrialised nations, and these could be similarly generated.

While the present invention has been specifically described with respect to separation and recovery of carbon dioxide and hydrogen sulphide from a sour natural gas, it will be appreciated that the present invention may be readily used to separate and recover hydrogen sulphide and mercaptans from sour gas from various sources, e.g. landfill gas. Additionally, the present invention may be readily adapted to separate and recover hydrogen sulphide and mercaptans from crude oil or petroleum condensates.

In the description of the invention, except where the context requires otherwise due to express language or necessary implication, the words "comprise" or variations such as "comprises" or "comprising" are used in an inclusive sense, i.e. to specify the presence of the stated features, but not to preclude the presence or addition of further features in various embodiments of the invention.

It is to be understood that, although prior art use and publications may be referred to herein, such reference does not constitute an admission that any of these form a part of the common general knowledge in the art, in Australia or any other country.

Numerous variations and modifications will suggest themselves to persons skilled in the relevant art, in addition to those already described, without departing from the basic inventive concepts. All such variations and modifications are to be considered within the scope of the present invention, the nature of which is to be determined from the foregoing description.

The invention claimed is:

1. A process for recovering methane and ethane from a sour hydrocarbon gas, the process comprising the steps of:
   a) mixing the sour hydrocarbon gas with an azeotrope inhibitor agent comprising 1,1-dimethylhydrazine or ethylene oxide; and
   b) passing the mixture into a first distillation column and operating the first distillation column under a first set of temperature and pressure conditions in which the methane and ethane are separated from the mixture as a first overhead vapour product.

2. The process according to claim 1, further comprising separating a sour species from a bottoms liquid product of the first distillation column.

3. The process according to claim 2, wherein the step of separating the sour species from said bottoms liquid product comprises passing said bottoms liquid product into a second distillation column and operating said second distillation column under a second set of temperature and pressure conditions in which the sour species is separated from the bottoms liquid product as a second overhead vapour product.

4. The process according to claim 2, wherein the step of separating the sour species from said bottoms liquid product comprises reducing the pressure of the bottoms liquid product to a pressure at which the sour species is separated from the bottoms liquid product in a vapour phase and said agent remains in a liquid phase.

5. The process according to claim 1, wherein the process further comprises separating hydrocarbons having 3 or more carbons from the sour hydrocarbon gas prior to mixing the agent with the sour hydrocarbon gas.

6. A process for recovering a sour species from a sour hydrocarbon gas, the process comprising the steps of:
   a) separating hydrocarbons having 3 or more carbons from the sour hydrocarbon gas;
   b) mixing the hydrocarbon-depleted gas with an azeotrope inhibitor agent comprising 1,1-dimethylhydrazine or ethylene oxide;
   c) passing the mixture into a first distillation column and operating said first distillation column under a first set of temperature and pressure conditions in which methane and ethane are separated from the mixture as a first overhead vapour product; and
   d) separating the sour species from a bottoms liquid product of the first distillation column.

7. The process according to claim 6, wherein separating hydrocarbons having 3 or more carbons comprises passing the sour hydrocarbon gas into a distillation column and operating said distillation column under a set of temperature and pressure conditions sufficient to separate hydrocarbons having 3 or more carbons as a liquid bottoms product of the distillation column.

8. The process according to claim 7, wherein said conditions are selected so that no more than about 0.2 mol % of hydrocarbons having 3 or more carbons remain in the overhead vapour product of said distillation.

9. The process according to claim 8, wherein said conditions are selected such that the concentration of sour species in the separated hydrocarbon stream is no more than about 0.01 mol %.

10. The process according to claim 6, wherein said hydrocarbon gas is mixed with about 1 mol % to about 40 mol % of the agent.

11. The process according to claim 6, wherein recovery of the methane and ethane from the first distillation column is greater than 80 mol %.

12. The process according to claim 6, wherein the separation of the sour species is greater than or equal to 90 mol %.

13. The process according to claim 6, wherein a purity of the separated sour species is about 90 mol % or greater.

14. The process according to claim 6, wherein the agent is mixed with the sour hydrocarbon gas prior to passing the mixture to the first distillation column, or the agent is mixed with the sour hydrocarbon gas within the first distillation column by introducing the sour hydrocarbon gas and the agent separately into the first distillation column.

15. The process according to claim 1, wherein said hydrocarbon gas is mixed with about 1 mol % to about 40 mol % of the agent.

16. The process according to claim 1, wherein recovery of the light hydrocarbon from the first distillation column is greater than 80 mol %.

17. The process according to claim 1, wherein the agent is mixed with the sour hydrocarbon gas prior to passing the mixture to the first distillation column, or the agent is mixed with the sour hydrocarbon gas within the first distillation column by introducing the sour hydrocarbon gas and the agent separately into the first distillation column.

18. A hydrocarbon separation system comprising:
   a sour hydrocarbon feedgas source;

an azeotrope inhibitor source comprising a source of 1,1-dimethylhydrazine or ethylene oxide;

a first chiller having an inlet and an outlet, wherein the first chiller inlet is in fluid communication with the feedgas source and the azeotrope inhibitor source;

a first distillation column having a top end and a bottom end, a first inlet disposed between the two ends, a vapor outlet adjacent the top end, a liquid outlet adjacent the bottom end and a second inlet adjacent the top end and a third inlet adjacent the bottom end, wherein the outlet of the first chiller is in fluid communication with the first inlet of the first distillation column;

a second chiller having an inlet and an outlet, wherein the second chiller inlet is in fluid communication with the vapor outlet of the first distillation column;

a first vapor-liquid separator having an inlet, a gas outlet and a liquid outlet, wherein the inlet of the first vapor-liquid separator is in fluid communication with the outlet of the second chiller and wherein the liquid outlet is in fluid communication with the second inlet of the first distillation column;

a first heat exchanger having an inlet and an outlet, wherein the inlet of the first heat exchanger is in fluid communication with the liquid outlet of the first distillation column and the outlet of the first heat exchanger is in fluid communication with the third inlet of the first distillation column;

a second distillation column having a top end and a bottom end, a first inlet disposed between the two ends, a vapor outlet adjacent the top end, a liquid outlet adjacent the bottom end and a second inlet adjacent the top end and a third inlet adjacent the bottom end, wherein the liquid outlet of the first distillation column is in fluid communication with the first inlet of the second distillation column;

a third chiller having an inlet and an outlet, wherein the third chiller inlet is in fluid communication with the vapor outlet of the second distillation column;

a second vapor-liquid separator having an inlet, a gas outlet and a liquid outlet, wherein the inlet of the second vapor-liquid separator is in fluid communication with the outlet of the third chiller and wherein the liquid outlet is in fluid communication with the second inlet of the second distillation column; and a second heat exchanger having an inlet and an outlet, wherein the inlet of the second heat exchanger is in fluid communication with the liquid outlet of the second distillation column and the outlet of the second heat exchanger is in fluid communication with the third inlet of the second distillation column, wherein the second distillation column is the azeotrope inhibitor source.

19. The system according to claim 18, wherein the liquid outlet of the second distillation column is in fluid communication with the inlet of the first chiller.

20. The system according to claim 18, wherein the sour hydrocarbon feedgas source is a distillation column.

\* \* \* \* \*